(12) United States Patent
Westman et al.

(10) Patent No.: US 8,557,843 B2
(45) Date of Patent: Oct. 15, 2013

(54) QUINOLINE DERIVATIVES AND THEIR USE AS TYROSINE KINASE INHIBITORS

(75) Inventors: Jacob Westman, Jarlasa (SE); Natalia Nekhotiaeva, Solna (SE); Johan Wannberg, Uppsala (SE); Ulrika Backman, Uppsala (SE); Johan Malm, Trangsund (SE)

(73) Assignee: ClanoTech AB, Solna (SE)

( * ) Notice: Subject to any disclaimer, the term of this patent is extended or adjusted under 35 U.S.C. 154(b) by 372 days.

(21) Appl. No.: 12/742,944

(22) PCT Filed: Nov. 14, 2008

(86) PCT No.: PCT/EP2008/065596
§ 371 (c)(1),
(2), (4) Date: May 14, 2010

(87) PCT Pub. No.: WO2009/063070
PCT Pub. Date: May 22, 2009

(65) Prior Publication Data
US 2011/0053976 A1    Mar. 3, 2011

Related U.S. Application Data

(60) Provisional application No. 60/988,147, filed on Nov. 15, 2007.

(30) Foreign Application Priority Data

Nov. 15, 2007  (EP) .................................... 07120799

(51) Int. Cl.
*A01N 43/42*     (2006.01)
*A61K 31/47*     (2006.01)
(52) U.S. Cl.
USPC ......................................... 514/313; 546/160
(58) Field of Classification Search
None
See application file for complete search history.

(56) References Cited

U.S. PATENT DOCUMENTS 5,650,415 A     7/1997  Tang et al.

FOREIGN PATENT DOCUMENTS

| WO | 0068201 A1 | 11/2000 |
| WO | 2007139496 A1 | 12/2007 |
| WO | 2008119771 A2 | 10/2008 |

OTHER PUBLICATIONS

Kim et al: "Putative therapeutic agents for the learning and memory deficits of people with Down syndrome", Bioorganic & Medicinal Chemistry Letters, 2006, pp. 3772-3776, vol. 16, Elsevier Ltd.
Sapelkin V M et al: "Search for protein kinase CK2 inhibitors among 3-carboxy-4-aminoquinoline derivatives", Ukrainica Bioorganica Acta, 2005, pp. 28-32, vol. 2, No. 1, Natsional 'Na Akademiya Nauk Ukrainy, Instytut Molekulyarnoi, UK, XP003018391.
International Search Report, Dated May 11, 2009, PCT/EP2008/065596.

*Primary Examiner* — Anna Pagonakis
(74) *Attorney, Agent, or Firm* — Young & Thompson

(57) ABSTRACT

A compound of formula (I)

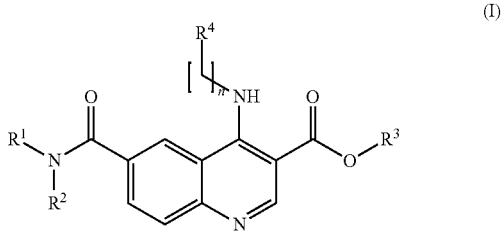

as well as pharmaceutically acceptable salts thereof. A pharmaceutical composition having a therapeutically effective amount of the compound. The compound is useful for the treatment of cancer, diabetic retinopathy, age-related macular degeneration, inflammation, stroke, ischemic myocardium, atherosclerosis, macular edema or psoriasis.

6 Claims, 5 Drawing Sheets

QUINOLINE DERIVATIVES AND THEIR USE AS TYROSINE KINASE INHIBITORS

FIELD OF THE INVENTION

The present invention relates to quinoline derivatives and to the use thereof in therapy. More particularly, the present invention relates to quinoline derivatives for the treatment of cancer, diabetic retinopathy, age-related macular degeneration, inflammation, stroke, ischemic myocardium, atherosclerosis, macular edema and psoriasis.

BACKGROUND OF THE INVENTION

Angiogenesis, the outgrowth of new capillaries from pre-existing vessels, is essential for embryonic development, organ formation, tissue regeneration, and remodeling [Folkman, J. & Shing, Y. (1992) *J. Biol. Chem.* 267, 10931-10934]. It also contributes to the development and progression of a variety of pathological conditions, including tumor growth and metastasis, cardiovascular diseases, diabetic retinopathy, rheumatoid arthritis, and psoriasis [Folkman, J. (1995) *Nat. Med.* 1, 27-312]. Angiogenesis and vasculogenesis are complex multistep processes that include proliferation, migration and differentiation of endothelial cells, degradation of the extracellular matrix, tube formation, and sprouting of new capillary branches [Hanahan, D. & Folkman, J. (1996) *Cell* 86, 353-364; Risau, W. (1997) *Nature (London)* 386, 671-674]. The complexity of the angiogenic processes suggests the existence of multiple controls of the system, which can be transiently switched on and off. A switch of the angiogenic phenotype in tissues is thought to depend on a local change of the balance between angiogenic stimulators and inhibitors [Folkman, J. (1995) *N. Engl. J. Med.* 333, 1757-1763].

Among many described angiogenic factors, vascular endothelial growth factor (VEGF)/vascular permeability factor is one of the best-characterized positive regulators with its distinct specificity for vascular endothelial cells [Senger, D. R., Galli, S. J., Dvorak, A. M., Perruzzi, C. A., Harvey, V. S. & Dvorak. H. F. (1983) *Science* 219, 983-985; Ferrara, N. & Henzel, W. J. (1989) *Biochem. Biophys. Res. Commun.* 161, 851-858; Gospodarowicz, D., Abraham, J. A. & Schilling, J. (1989) *Proc. Natl. Acad. Sci. USA* 86, 7311-7315]. The biological actions of VEGF include stimulation of endothelial cell proliferation, migration, differentiation, tube formation, increase of vascular permeability, and maintenance of vascular integrity [Mustonen, T. & Alitalo, K. (1995) *J. Cell Biol.* 129, 895-898; Ferrara, N. & Davis-Smyth, T. (1997) *Endocr. Rev.* 18, 4-25; Thomas, K. (1996) *J. Biol. Chem.* 271, 603-606; Risau, W. (1997) *Nature (London)* 386, 671-674; Breier, G. & Risau, W. (1997) *Trends Cell Biol.* 6, 454-456]. The angiogenic responses induced by VEGF are mediated by tyrosine kinase receptors, which are expressed primarily on vascular cells of the endothelial lineage [Mustonen, T. & Alitalo, K. (1995) *J. Cell Biol.* 129, 895-898; De Vries, C., Escobedo, J. A., Ueno, H., Huck, K., Ferrara, N. & Williams, L. T. (1992) *Science* 255, 989-99; Terman, B. I., Dougher-Vermazen, M., Carrion, M. E., Dimitrov, D., Armellino, D. C., Gospodorawicz, D. & Bohlen, P. (1992) *Biochem. Biophys. Res. Commun.* 187, 1579-1586].

Inhibition of cell adhesion to the endothelial cell membrane (ECM), the fundamental step for activation, survival, targeting and migration of activated endothelial cells, might be one of the most promising target mechanisms for anti-angiogenesis. Not only VEGF is involved in these mechanisms but many of these interactions are also mediated by integrins, a family of multifunction cell adhesion receptors.

Members of the integrin family are non-covalently alpha/beta heterodimers that mediate cell-cell, cell-extracellular matrix and cell-pathogen interactions. Until now, 19 different integrin alpha subunits and 8 different beta subunits are known that combine to form at least 25 different alpha/beta heterodimers with different ligand specificity. The ligands for the extracellular domain of many integrins are the proteins of the extracellular matrix and the intracellular domain of the integrins are either directly or indirectly connected to intracellular components such as kinases and the cytoskeleton. Integrins serve as bidirectional signalling receptors, whereby protein activities and gene expression are changed by integrins in response to ligand binding to the extracellular domain thereof, which is also referred to as outside-in-signalling. On the other hand, the affinity of the integrins is modulated in response to intracellular changes such as binding of proteins to the extracellular domain of the integrin, which is referred to as inside-out signalling [Humphries (2000) *Biochem Soc Trans.* 28, 311; Hynes (2002) *Cell,* 110, 673].

Several studies on the integrin pattern on activated endothelial cells, mice gene knockouts and inhibition studies in angiogenic animal models with antibodies, peptides and small molecules have provided information about integrins and ECM proteins involved in critical steps of angiogenesis [Brooks (1994) *Science,* 264, 569; Brooks (1996) *Eur J Cancer,* 32A, 2423; Mousa (2002), *Curr Opin Chem Biol,* 6, 534; Hynes (2002) *Nature Medicine,* 8, 918; Kim (2000) *Am J Pathol,* 156, 1345]. From this work it appeared that the fibronectin receptors alpha-v-beta-3, alpha-v-beta-5 and the fibronectin receptor alpha5beta1 play a critical role in angiogenesis. Alpha5beta1 expression is significantly upregulated in blood vessels in human tumors and after stimulation with growth factors and, once expressed, alpha-5-beta-1 regulates the survival and migration of endothelial cells in vitro and in vivo.

SUMMARY OF THE INVENTION

According to experiments performed by the present inventors only inhibition of the fibronectin receptor alpha-5-beta-1 has so far produced biological data that are fully consistent with its proposed role in angiogenesis. Therefore, without wishing to be bound to any theory, it is contemplated that alpha-5-beta-1 might be a preferred target for the development of anti-angiogenic drugs, and consequently may have a great therapeutic potential for the treatment of neovascularisation in tumors, in the eye and in inflammatory processes.

The present inventors now have found that novel quinoline derivatives with certain side-chains pattern are effectively capable of blocking integrins, and potentially tyrosine kinases, in particular the fibronectin receptor alpha-5-beta-1.

Compared to similar analogs in the field, the compounds of the present invention also have improved solubility properties.

Consequently, according to one aspect, the present invention relates to a compound of formula (I)

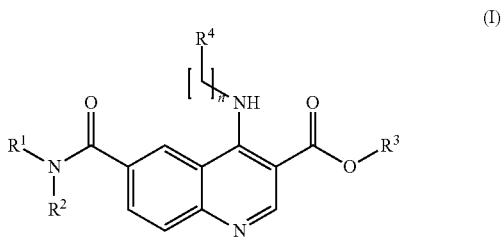

(I)

wherein:

n=0, 1 or 2;

$R^1$ and $R^2$ are independently selected from hydrogen, saturated or unsaturated, branched or unbranched $C_{1-10}$ alkyl or $C_{3-12}$ cycloalkyl; and substituted or non-substituted phenyl or benzyl;

$R^3$ is hydrogen;

$R^4$ is substituted or non-substituted $C_6$-$C_{10}$ aryl or $C_1$-$C_9$ heteroaryl wherein the heteroatoms independently are selected from N, O and S; or substituted or non-substituted mono- or bicyclic $C_{3-12}$ cycloalkyl or $C_1$-$C_9$ heterocyclyl wherein the heteroatoms are independently selected from N, O and S;

as well as pharmaceutically acceptable salts thereof.

According to a further aspect the invention relates to a compound of formula (I) as defined herein above, or a pharmaceutically acceptable salt thereof, for use in therapy.

According to a further aspect, the present invention relates to a compound of formula (I) or pharmaceutically acceptable salts thereof, for use in the treatment of diseases such as cancer, diabetic retinopathy, age-related macular degeneration, chronic inflammation, stroke, ischemic myocardium, atherosclerosis, tumor growth and macular edema.

According to still a further aspect, the present invention relates to the use of a compound of formula (I) or pharmaceutically acceptable salts thereof, for manufacturing a medicament for the treatment of diseases such as cancer, diabetic retinopathy, age-related macular degeneration, chronic inflammation, stroke, ischemic myocardium, atherosclerosis, tumor growth and macular edema.

According to another aspect, the invention provides a method of treatment of a disorder selected from cancer, diabetic retinopathy, age-related macular degeneration, chronic inflammation, stroke, ischemic myocardium, atherosclerosis, tumor growth and macular edema by administration of a therapeutically effective amount of a compound of formula (I) or a pharmaceutically acceptable salt thereof to a mammal in need of such treatment.

Further aspects and embodiments of the invention are as defined in the claims.

DETAILED DESCRIPTION OF THE INVENTION

Figure 1:
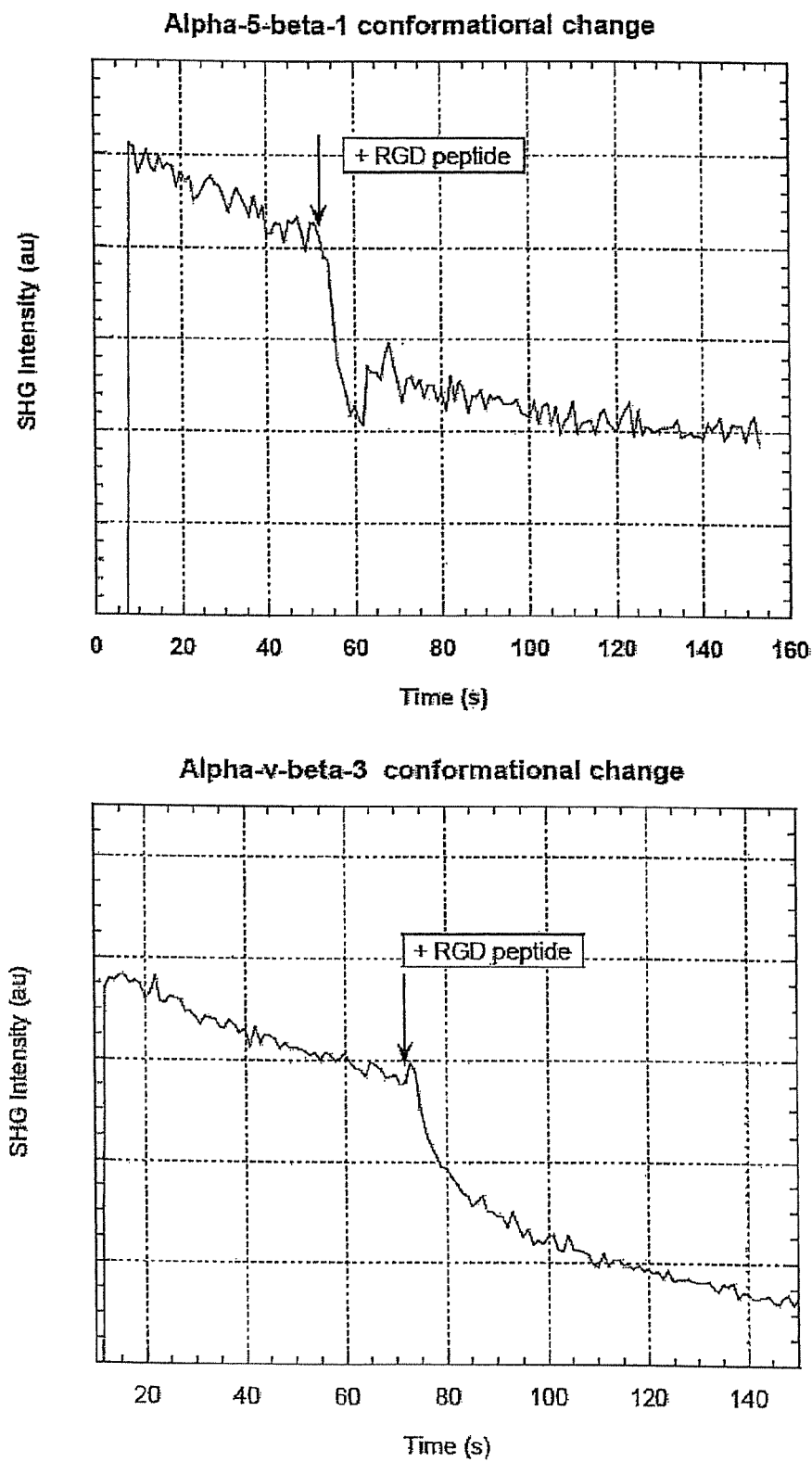
FIG. 1 is a plot of the SHG signal as a function of time, obtained from labeled alpha-5-beta-1 receptor (upper) and alpha-v-beta-3 (lower) and a peptide derived from fibronectin, showing the conformational change of the receptor.

The present invention relates to quinoline-3-carboxylic acid derivatives, which can be utilized to treat diseases and conditions such as cancer, diabetic retinopathy, age-related macular degeneration, inflammation, stroke, ischemic myocardium, atherosclerosis, macular edema, psoriasis, and the like in mammals.

The preparation of the compounds of the invention lies well within the capability of the person skilled in the art. As an example, a quinoline-3-carboxylic acid ester may be formed in a four step procedure wherein, first, a suitable aniline derivative is reacted with a suitable mono- or diethyl ester, the formed intermediate cyclized to give a quinolin-4-ol derivative, which is then converted to the corresponding halogen derivative and finally reacted with a suitable amine to form a quinoline-3-carboxylic acid ester. The quinoline-3-carboxylic acid ester then is hydrolysed to give the corresponding acid. The entire synthesis is illustrated by Reaction Scheme 1.

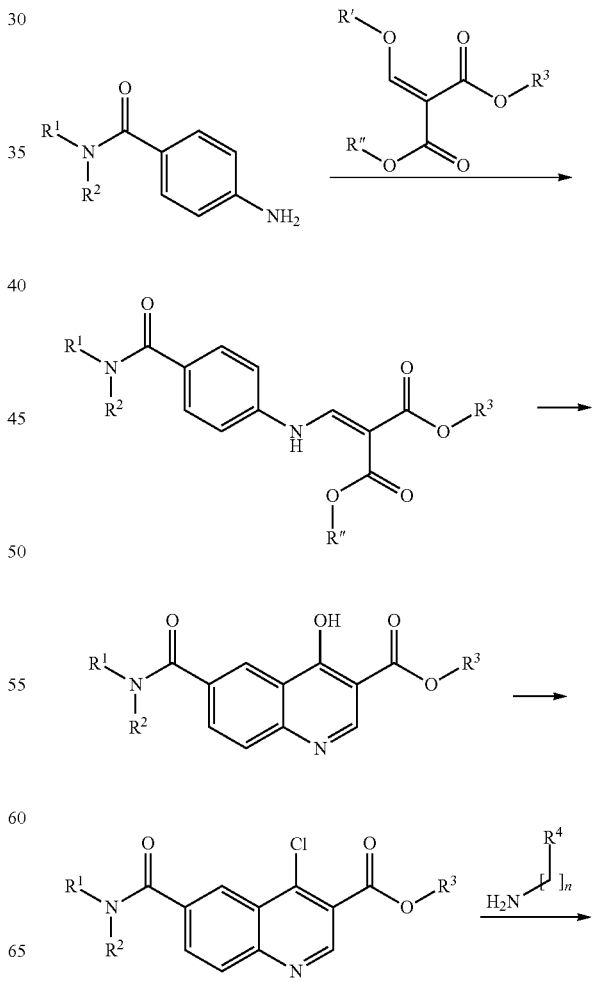

Reaction Scheme 1

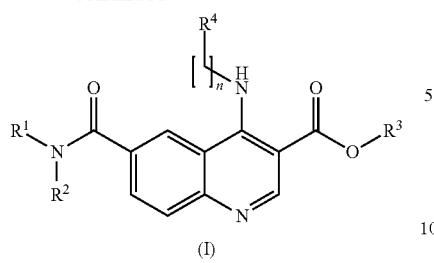

(I)

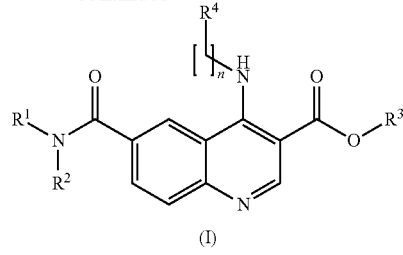

(I)

With regard to the above reaction sequence, it is well within the capability of the person skilled in the art to select suitable reaction components as well as reaction conditions.

Another synthetic method useful for preparing the inventive compounds is illustrated in Reaction Scheme 2. In this case the synthesis is started from p-bromoaniline and the amide group is introduced in the last step.

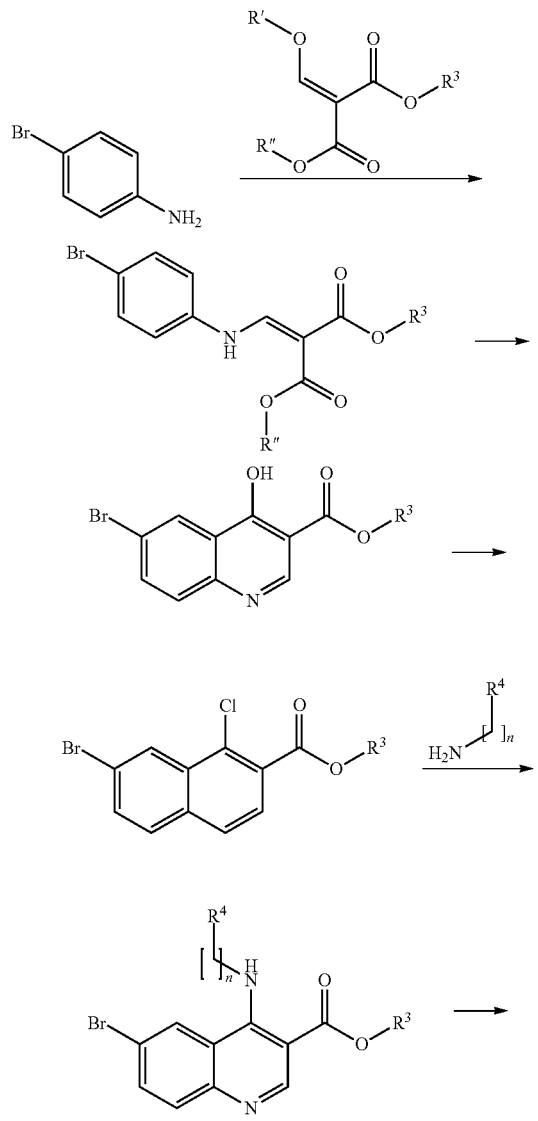

In summary, there are several ways in which order to introduce the groups $R^1$, $R^2$, $R^3$ and $R^4$, all well known for the one skilled in the art, in order to arrive to the compounds of the invention.

The term "alkyl" as employed herein alone or as part of another group refers to an acyclic straight or branched chain radical, containing 1, 2, 3, 4, 5, 6, 7, 8, 9 or 10 carbons in the normal chain, i.e. methyl, ethyl, propyl, butyl, pentyl, hexyl, heptyl, octyl, nonyl, decyl. The alkyl group preferably contains 1, 2, 3 or 4 carbons in the normal chain that also can be substituted with 1, 2 or 3 groups of halogen, which groups may be the same or different at any available point, as defined with respect to each variable. When such a substituted alkyl group is present, the preferred halogen is fluorine, such as in —$CF_3$, —$CHF_2$, —$CH_2F$, —$CHFCH_2F$, and the like.

Unless otherwise indicated, the term "lower alkyl" as employed herein as part of another group includes both straight and branched chain hydrocarbons, saturated or unsaturated, containing 1, 2, 3 or 4 carbons, such as methyl, ethyl, propyl, isopropyl, butyl, t-butyl, or isobutyl.

As noted herein above, the alkyl groups considered may be unsaturated (alkenyl or alkynyl)hydrocarbyl radicals The term "alkenyl" as used herein by itself or as part of another group refers to straight or branched chain radicals of 2, 3, 4, 5, 6, 7, 8, 9 or 10 carbons, which contains at least one carbon to carbon double bond. Preferably one carbon to carbon double bond is present, such as in the normal chain vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, and the like. The alkenyl group preferably contains 2, 3 or 4 carbons in the normal chain. The straight or branched portion of the alkenyl group may be optionally substituted by 1, 2 or 3 halogens, which halogens may be the same or different, the preferred halogen being fluorine.

The term "alkynyl" as used herein by itself or as part of another group refers to straight or branched chain radicals of 2, 3, 4, 5, 6, 7, 8, 9 or 10 carbons and at least one carbon to carbon triple bond. Preferably, one carbon to carbon triple bond is present in the normal chain such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl, and the like. The alkynyl group preferably contains 1, 2, 3 or 4 carbons in the normal chain. The straight portion of the alkynyl group may be optionally substituted by 1, 2 or 3 groups of halogen, which halogens may be the same or different, the preferred halogen being fluorine.

The term "cycloalkyl" as employed herein alone or as part of another group includes saturated cyclic hydrocarbyl groups or partially unsaturated (containing 1 or 2 double bonds) cyclic hydrocarbyl groups, containing one ring and a total of 3, 4, 5, 6, 7, 8, 9, 10, 11 or 12 carbons, preferably 3 or 4 carbons, forming the ring, which includes cyclopropyl, cyclobutyl, cyclopentyl, cyclohexyl, cycloheptyl, cyclopentenyl, cyclohexenyl, and the like. The cyclic hydrocarbyl may be mono-, bi- or tricyclic. The cycloalkyl group may be optionally substituted by 1, 2 or 3 halogens, which may be the same or different, the preferred halogen being fluorine.

As used herein, and unless otherwise specified, the terms "heterocyclyl" mean a non-aromatic cyclic group containing one or more heteroatom(s) preferably selected from N, O and S, such as a aziridinyl, azetidinyl, dihydropyranyl, dihydropyridyl, dihydropyrrolyl, dioxolanyl, dioxanyl, dithianyl, dithiolanyl, imidazolidinyl, imidazolinyl, morpholinyl, oxetanyl, oxiranyl, pyrrolidinyl, pyrrolidinonyl, piperidyl, piperazinyl, piperidinyl, pyrazolidinyl, quinuclidinyl, sulfalonyl, 3-sulfolenyl, tetrahydrofuranyl tetrahydropyranyl, tetrahydropyridyl, thietanyl, thiiranyl, thiolanyl, thiomorpholinyl, trithianyl, tropanyl, monosaccharide and the like.

The term "halogen" refers to fluorine, chlorine, bromine and iodine.

As used herein, the term "aryl" means an aromatic group, such as phenyl or naphthyl, and the like.

As used herein, the term "heteroaryl" means a mono-, bi-, or tricyclic heteroaromatic group containing one or more heteroatom(s) preferably selected from N, O and S, such as pyridyl, quinolinyl, furanyl, thienyl, oxadiazolyl, thiadiazolyl, thiazolyl, oxazolyl, pyrazolyl, triazolyl, tetrazolyl, isoxazolyl, isothiazolyl, isoquinolinyl, naphthyridinyl, imidazolyl, phenazinyl, phenothiazinyl, phthalazinyl, indolyl, pyridazinyl, quinazolinyl, quinolizinyl, quinoxalinyl, tetrahydroisoquinolinyl, pyrazinyl, indazolyl, indolinyl, pyrimidinyl, thiophenetyl, pyranyl, carbazolyl, chromanyl, cinnolinyl, acridinyl, benzimidazolyl, benzodioxanyl, benzodioxepinyl, benzodioxolyl, benzofuranyl, benzothiazolyl, benzobenzoxadiazolyl, benzoxazinyl, benzoxazolyl, benzomorpholinyl, benzoselenadiazolyl, benzothienyl, purinyl, pteridinyl and the like.

As used herein, and unless specified otherwise, the term "substituted" means that the entity is substituted with at least one moiety selected from saturated or unsaturated, branched, unbranched or cyclic lower alkyl, hydroxyl, amine, sulfide, silyl, halogen, nitrile, carboxylic acid, sulfonic acid, lower alkoxy, lower alkyl secondary or tertiary amine, lower alkyl amides, lower alkyl ethers, lower alkyl ketone, lower alkyl sulphide, lower alkyl carboxylic acid esters, lower alkyl sulfonic acid ester, lower alkyl sulfone, lower alkyl sulfoxide, lower alkyl sulphonamide, lower alkyl alcohol, lower alkyl acetyl, lower dialkyl disulfide, and the like.

Thus, according to a first aspect, the invention relates to a compound of formula (I)

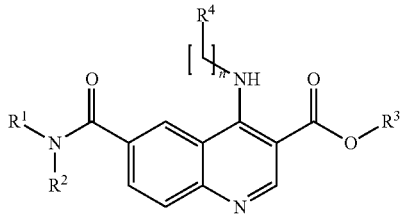

wherein:
n=0, 1 or 2; preferably n is 0 or 1, more preferably n is 0;
$R^1$ and $R^2$ are independently selected from hydrogen, saturated or unsaturated, branched or unbranched $C_{1-10}$ alkyl or $C_{3-12}$ cycloalkyl, and substituted or non-substituted phenyl or benzyl;
$R^3$ is hydrogen;
$R^4$ is substituted or non-substituted $C_6$-$C_{10}$ aryl or $C_1$-$C_9$ heteroaryl wherein the heteroatoms independently are selected from N, O and S; or substituted or non-substituted mono- or bicyclic $C_{3-12}$ cycloalkyl or $C_1$-$C_9$ heterocyclyl wherein the heteroatoms are independently selected from N, O and S;

as well as pharmaceutically acceptable salts thereof.

In one embodiment of the invention, $R^1$ and $R^2$ are independently selected from hydrogen and saturated or unsaturated, branched or unbranched $C_{1-10}$ alkyl or $C_{3-12}$ cycloalkyl, e.g. from hydrogen and saturated or unsaturated, branched or unbranched $C_{1-6}$ alkyl or $C_{3-6}$ cycloalkyl, e.g. $C_{1-4}$ alkyl and $C_{3-4}$ cycloalkyl, in particular saturated $C_{1-4}$ alkyl and $C_{3-4}$ cycloalkyl. For example, $R^1$ and $R^2$ may be independently selected from hydrogen and saturated or unsaturated, branched or unbranched $C_{1-6}$ alkyl, such as from hydrogen and saturated or unsaturated, branched or unbranched $C_{1-4}$ alkyl, in particular hydrogen and saturated $C_{1-4}$ alkyl, e.g. hydrogen, methyl, ethyl and propyl, in particular hydrogen and methyl.

In one embodiment, at least one of $R^1$ and $R^2$ is not hydrogen. In one embodiment, $R^1$ is hydrogen and $R^2$ is not hydrogen.

In the inventive compounds of formula (I), $R^4$ is substituted or non-substituted $C_6$-$C_{10}$ aryl or $C_1$-$C_9$ heteroaryl wherein the heteroatoms independently are selected from N, O and S; or substituted or non-substituted mono- or bicyclic $C_{3-12}$ cycloalkyl or $C_1$-$C_9$ heterocyclyl wherein the heteroatoms are independently selected from N, O and S. In one embodiment, $R^4$ is substituted or non-substituted $C_6$-$C_{10}$ aryl or $C_1$-$C_9$ heteroaryl wherein the heteroatoms independently are selected from N, O and S; in particular $R^4$ is substituted or non-substituted $C_6$-$C_{10}$ aryl, e.g. substituted or non-substituted phenyl.

Thus, in one embodiment, the compound of formula (I) may be represented by the formula (I')

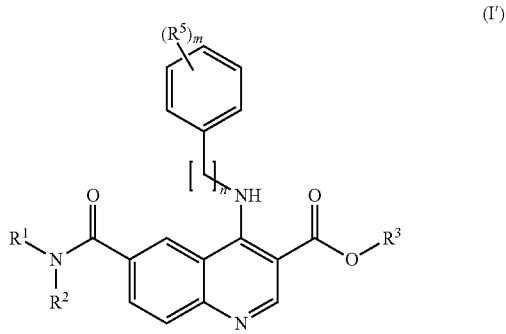

wherein $R^1$, $R^2$, $R^3$ and n are as defined herein above, m is 0-5, e.g. 1-3, or 1-2, in particular 1; and $R^5$ is a substituent as defined herein above, and preferably is selected from preferably saturated C1-C6 alkyl and C1-C6 alkoxy, more preferably C1-C4 alkyl and C1-C4 alkoxy, e.g. C1-C3 alkyl and C1-C3 alkoxy, such as methyl, ethyl, methoxy and ethoxy, e.g. methyl and methoxy.

In one embodiment, in a compound of formula (I'), m is 0 or 1, e.g. 1.

In one particular embodiment, in a compound of formula (I'), m is 1 and $R^5$ is in para position, i.e. the compound of the invention may be represented by formula (I")

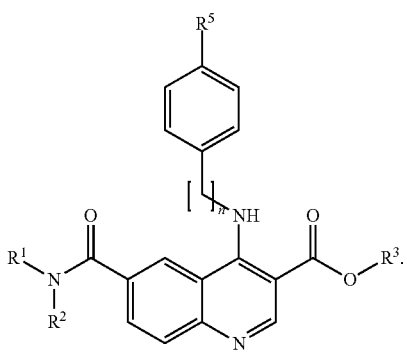

(I")

wherein $R^1$, $R^2$, $R^3$, $R^5$ and n are as defined herein above.

In one embodiment, the compound is selected from 6-(methylcarbamoyl)-4-[(4-methylphenyl)amino]quinoline-3-carboxylic acid and 4-[(4-methoxyphenyl)amino]-6-(methylcarbamoyl)quinoline-3-carboxylic acid, or a pharmaceutically acceptable salt thereof.

It should be understood, that, unless the contrary is indicated or apparent from the context, any reference made herein to a compound of formula (I) also is intended to refer to a compound of formula (I') or (I"), which are both embodiments comprised within the scope of formula (I).

The compounds of the invention can be present as salts, which are also within the scope of this invention. Pharmaceutically acceptable (i.e., non-toxic, physiologically acceptable) salts are preferred.

For example, the inventive compounds can form acid addition salts, e.g. at the amino function. These may be formed, for example, with strong inorganic acids, such as mineral acids, for example sulfuric acid, phosphoric acid or a hydrohalic acid; strong organic carboxylic acids, such as alkanecarboxylic acids of 1 to 4 carbon atoms which are unsubstituted or substituted, for example, by halogen, for example acetic acid, saturated or unsaturated dicarboxylic acids, for example oxalic, malonic, succinic, maleic, fumaric, phthalic or terephthalic acid, hydroxycarboxylic acids, for example ascorbic, glycolic, lactic, malic, tartaric or citric acid, amino acids, (for example aspartic or glutamic acid or lysine or arginine), or benzoic acid, or with organic sulfonic acids, such as ($C_1$-$C_4$) alkyl or arylsulfonic acids which are unsubstituted or substituted, for example by halogen, for example methyl- or p-toluene-sulfonic acid. Corresponding acid addition salts can also be formed having, if desired, an additionally present basic center.

The compounds of formula I having at least one acid group (for example COOH) can also form salts with bases. Suitable salts with bases are, for example, metal salts, such as alkali metal or alkaline earth metal salts, for example sodium, potassium or magnesium salts, or salts with ammonia or an organic amine, such as morpholine, thiomorpholine, piperidine, pyrrolidine, a mono-, di- or tri-lower alkylamine, for example ethyl, tertbutyl, diethyl, diisopropyl, triethyl, tributyl or dimethyl-propylamine, or a mono, di or trihydroxy lower alkylamine, for example mono-, di- or triethanolamine. Corresponding internal salts may furthermore be formed. Salts that are unsuitable for pharmaceutical uses but which can be employed, for example, for the isolation or purification of free compounds of formula I or their pharmaceutically acceptable salts are also included.

An administration of a therapeutic agent of the invention includes administration of a therapeutically effective amount of the agent of the invention. The term "therapeutically effective amount" as used herein refers to an amount of a therapeutic agent to treat or prevent a condition treatable by administration of a composition of the invention. That amount is the amount sufficient to exhibit a detectable therapeutic or preventative or ameliorative effect. The effect may include, for example, treatment or prevention of the conditions listed herein. The precise effective amount for a subject will depend upon the subject's size and general condition, the nature and extent of the condition being treated, recommendations of the treating physician, and the therapeutics or combination of therapeutics selected for administration. Thus, it is not useful to exactly specify an exact effective amount in advance. In the case of oral administration the dosage might, however, vary from about 0.01 mg to about 1000 mg per day of a compound of formula (I) or the corresponding amount of a pharmaceutically acceptable salt thereof.

The composition according to the invention may be prepared for any route of administration, e.g. oral, intravenous, cutaneous or subcutaneous, nasal, intramuscular, or intraperitoneal. The precise nature of the carrier or other material will depend on the route of administration. For parenteral administration, a parenterally acceptable aqueous solution is employed, which is pyrogen free and has requisite pH, isotonicity and stability. Those skilled in the art are well able to prepare suitable solutions and numerous methods are described in the literature.

The pharmaceutically acceptable excipients described herein, for example, vehicles, adjuvants, carriers or diluents, are well-known to those who are skilled in the art and are readily available to the public. The pharmaceutically acceptable carrier may be one that is chemically inert to the active compounds and that has no detrimental side effects or toxicity under the conditions of use. Examples of pharmaceutical formulations can be found in Remington: The Science and Practice of Pharmacy. A. R. Gennaro, Editor. Lippincott, Williams and Wilkins, 20th edition (2000).

All stereoisomers of the compounds of the present invention are contemplated, either in admixture or in pure or substantially pure form. The compounds of the present invention can have asymmetric centers at any of the carbon atoms including any one of the R substituents. Consequently, compounds of formula I can exist in enantiomeric or diastereomeric forms or in mixtures thereof. The processes for preparation can utilize racemates, enantiomers or diastereomers as starting materials. When diastereomeric or enantiomeric products are prepared, they can be separated by conventional methods, which for example is chromatographic or fractional crystallization.

The compounds according to formula (I) will be useful for treating various diseases such as cancer, diabetic retinopathy, age-related macular degeneration, inflammation, stroke, ischemic myocardium, atherosclerosis, macular edema and psoriasis. The treatment may be preventive, palliative or curative.

The compounds of the present invention may be used or administered in combination with one or more additional drugs useful in the treatment of hyperproliferative diseases, e.g. a cytostatic agent. The components may be in the same formulation or in separate formulations for administration simultaneously or sequentially. The compounds of the present invention may also be used or administered in combination with other treatment such as irradiation for the treatment of cancer. Examples of cytostatic agents for use as indicated herein above are DNA alkylating compounds, topoisomerase I inhibitors, topoisomerase II inhibitors, compounds interfering with RNA and DNA synthesis, compounds polymerising the cytoskeleton, and compounds depolymerising the cytoskeleton.

The invention is illustrated by the following non-limiting Examples.

EXAMPLES

Example 1

Ethyl 6-(methylcarbamoyl)-4-[(4-methylphenyl)amino]quinoline-3-carboxylate. (Intermediary Product)

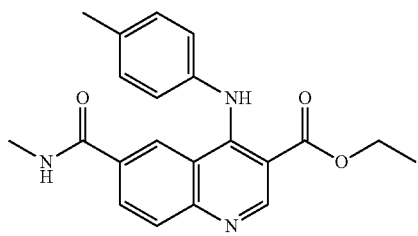 [SMILES: CCOC(=O)c1cnc2ccc(C(=O)NC)cc2c1Nc1ccc(C)cc1]

(a) Preparation of Intermediary Compound 2-[(4-bromophenylamino)methylene]malonic Acid Diethyl Ester

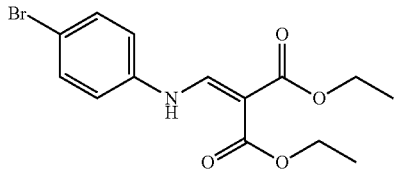 [SMILES: CCOC(=O)C(=CNc1ccc(Br)cc1)C(=O)OCC]

A 20 mL microwave vial was charged with 4-bromoaniline (6.881 g, 40.0 mmol), diethyl ethoxymethylenemalonate (8.650 g, 40.0 mmol) and toluene (5 mL). The vial was capped and the mixture was microwave heated at 150° C. for 30 min. After cooling, the solution was poured onto 50 mL of vigorously stirred iso-hexane. A thick, white precipitate formed and the suspension was stirred for another 15 min. The suspension was filtered and the product washed with 20 mL of iso-hexane. The product was dried under vacuum to give 11.678 g (85%) of 2-[(4-bromo-phenylamino)methylene]malonic acid diethyl ester. MS (ESI$^+$) m/z 342, 344 (MH$^+$).

(b) Preparation of Intermediary Compound 6-bromo-4-chloroquinoline-3-carboxylic Acid Ethyl Ester

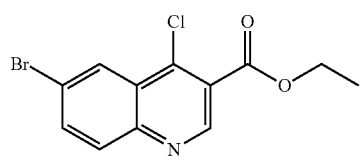

A 20 mL microwave vial was charged with 2-[(4-bromophenylamino)methylene]malonic acid diethyl ester (1.711 g, 5.0 mmol) and POCl$_3$ (phosphoryl chloride, 10.0 mL, 16.8 g, 109 mmol). The vial was capped and the mixture was microwave heated stepwise up to 180° C. (watching the pressure) over 5 min and then kept at 180° C. for 30 min Excess POCl$_3$ was evaporated and the residue partitioned between CH$_2$Cl$_2$ (40 mL) and 2 N NaOH (aq) (40 mL). The aqueous layer was extracted with CH$_2$Cl$_2$ (2×40 mL). The organic layers were combined, dried with Na$_2$CO$_3$ and evaporated. The residue was purified on column (silica gel, CH$_2$Cl$_2$ as eluent). Pure fractions were pooled, evaporated and the residue dried under vacuum to give 0.821 g (52%) of 6-bromo-4-chloroquinoline-3-carboxylic acid ethyl ester. MS (ESI$^+$) m/z 314, 316 (MH$^+$).

(c) Preparation of the Intermediary Compound 6-bromo-4-p-tolyl-aminoquinoline-3-carboxylic Acid Ethyl Ester

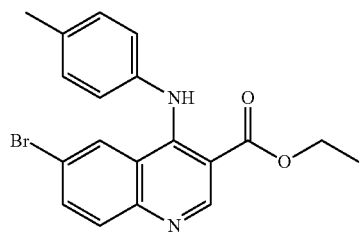 [SMILES: CCOC(=O)c1cnc2ccc(Br)cc2c1Nc1ccc(C)cc1]

A 20 mL microwave vial was charged with 6-bromo-4-chloro-quinoline-3-carboxylic acid ethyl ester (0.786 g, 2.50 mmol), p-toluidine (0.268 g, 2.50 mmol) and dry 1,4-dioxane (15 mL). The vial was capped and the mixture was microwave heated at 150° C. for 30 min. After cooling, a yellow precipitate had formed. The suspension was poured onto 2 N NaOH (aq) (100 mL) and the aqueous layer was extracted with CH$_2$Cl$_2$ (3×80 ml). The organic layers were combined and washed with H$_2$O (100 mL), dried with MgSO$_4$ and evaporated. The residue was purified on column (silica gel, iso-hexane/EtOAc 1:1). Pure fractions were combined, evaporated and the residue was dried under vacuum to give 0.748 g (78%) of 6-bromo-4-p-tolyl-aminoquinoline-3-carboxylic acid ethyl ester. MS (ESI$^+$) m/z 385, 387 (MH$^+$).

(d) A 2-mL microwave vial was charged with 6-bromo-4-p-tolyl-aminoquinoline-3-carboxylic acid ethyl ester (0.100 mmol), Herrmann's palladacycle (trans-di(μ-acetato)-bis[o-(di-o-tolylphosphino)benzyl]dipalladium(II), 4.7 mg, 0.0050 mmol), [(t-Bu)$_3$PH]BF$_4$ (5.9 mg, 0.020 mmol), Mo(CO)$_6$ (52.8 mg, 0.20 mmol), 1.5 equiv. of methylamine (2 M in THF) and dry THF (1.0 mL). Finally, DBU (1,8-Diazabicyclo[5.4.0]undec-7-ene, 0.045 μL, 0.30 mmol) was added and the vial was immediately capped with a Teflon septum and irradiated with microwaves for 5 min at 130° C. Volatiles were removed under reduced pressure and the residue purified by column chromatography to give ethyl 6-(methylcarbamoyl)-4-[(4-methylphenyl)amino]-quinoline-3-carboxylate.

Example 2

6-Methylcarbamoyl-4-p-tolylamino-quinoline-3-carboxylic Acid

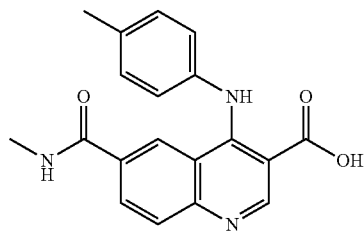 [SMILES: CNC(=O)c1ccc2ncc(C(=O)O)c(Nc3ccc(C)cc3)c2c1]

Ethyl 6-(methylcarbamoyl)-4-[(4-methylphenyl)amino] quinoline-3-carboxylate was hydrolysed under basic conditions using NaOH (aq.). The final product was purified by column chromatography.

Example 3

Ethyl 4-[(4-methoxyphenyl)amino]-6-(methylcarbamoyl)quinoline-3-carboxylate. (Intermediary Product)

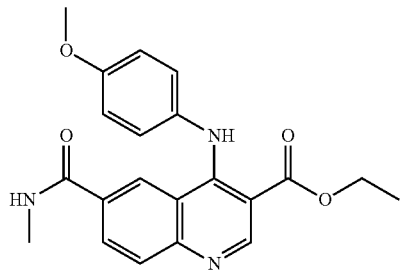 [SMILES: CCOC(=O)c1cnc2ccc(C(=O)NC)cc2c1Nc1ccc(OC)cc1]

(a) Preparation of Intermediary Compound 2-[(4-bromophenylamino)methylene]malonic Acid Diethyl Ester

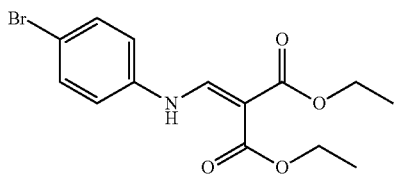 [SMILES: CCOC(=O)C(=CNc1ccc(Br)cc1)C(=O)OCC]

4-Bromoaniline (10 g, 0.058 mol) and 12.58 g of diethoxymethylene malonate (1 equiv.) were heated at 150° C. for 3 h in a sealed tube. The reaction mixture was then cooled and diluted with hexane when the solid product precipitated out. This solid was filtered, washed several times with hexane and dried under vacuum to afford 17.8 g (89%) of 2-[(4-bromo-phenylamino)methylene]malonic acid diethyl ester. $^1$H NMR (300 MHz, CDCl$_3$) δ 11.03 (d, 1H, J=13 Hz, —NH—), 8.48 (d, 1H, J=13 Hz, —CH═C), 7.49 (m, 2H, aromatic), 7.10-7.01 (m, 2H, aromatic), 4.42-4.22 (m, 4H, —CH$_2$—CH$_3$), 1.45-1.26 (m, 6H, —CH$_2$—CH$_3$); LC-MS (m/z) 343.9 (M+1).

(b) Preparation of Intermediary Compound 6-bromo-4-chloroquinoline-3-carboxylic Acid Ethyl Ester

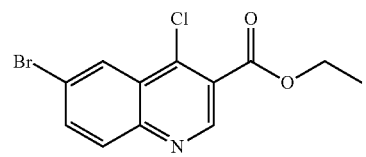 [SMILES: CCOC(=O)c1cnc2ccc(Br)cc2c1Cl]

2-[(4-Bromophenylamino)methylene]malonic acid diethyl ester (5 g) was heated with POCl$_3$ (phosphoryl chloride, 31.5 mL) at 150° C. in a sealed tube for about 6 h. The excess POCl$_3$ was removed by rotavapor and the crude mixture was diluted with dichloromethane. The dichloromethane extract was washed with 10% NaOH solution, dried over sodium sulphate and purified by column chromatography (Silica gel, hexane/ethyl acetate 80:20) to give 2.3 g (50%) of 6-bromo-4-chloroquinoline-3-carboxylic acid ethyl ester. $^1$H NMR (300 MHz, CDCl$_3$) δ 9.22 (s, 1H, aromatic), 8.60 (d, 1H, J=2.1 Hz, aromatic), 8.04 (d, 1H, J=9 Hz, aromatic), 7.95-7.85 (m, 1H, aromatic), 4.53 (q, 2H, J=7 Hz, —CH$_2$—), 1.50 (t, 3H, J=7 Hz, —CH$_3$); LC-MS (m/z) 315.8 (M+1).

(c) Preparation of Intermediary Compound Ethyl 6-bromo-4-[(4-methoxyphenyl)-amino]quinoline-3-carboxylate

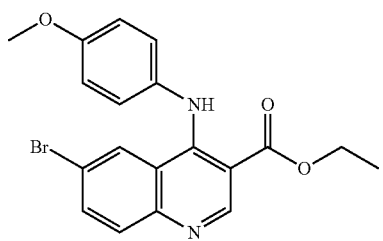 [SMILES: CCOC(=O)c1cnc2ccc(Br)cc2c1Nc1ccc(OC)cc1]

p-Anisidine (0.43 g) and 6-bromo-4-chloroquinoline-3-carboxylic acid ethyl ester (1 g) were mixed in dioxane and irradiated in a microwave reactor at 150° C. for 30 minutes. The reaction mixture was diluted with petroleum ether. The solid product obtained was filtered and dried to give 1.3 g (100%) of ethyl 6-bromo-4-[(4-methoxyphenyl)amino] quinoline-3-carboxylate. $^1$H NMR (300 MHz, CDCl$_3$) δ 11.41 (s, 1H, —NH—), 9.22 (s, 1H, aromatic), 8.20 (d, 1H, J=8.2 Hz, aromatic), 7.77 (d, 1H, J=8.2 Hz, aromatic), 7.64 (s, 1H, aromatic), 7.15 (d, 2H, J=8.1 Hz, aromatic), 6.99 (d, 2H, J=8.1 Hz, aromatic), 4.47 (q, 2H, J=7 Hz, —CH$_2$—), 3.89 (s, 3H, —OCH$_3$), 1.47 (t, 3H, J=7 Hz, —CH$_3$); LC-MS (m/z) 401.0 (M+1).

(d) Ethyl 6-bromo-4-[(4-methoxyphenyl)amino]quinoline-3-carboxylate (0.25 g, 0.623 mmol) was added to THF followed by Herrmann's palladacycle (trans-di(μ-acetato)-bis[o-(di-o-tolylphosphino)benzyl]dipalladium(II), 0.031 mmol), [(t-Bu)$_3$PH]BF$_4$ (tri tertiarybutyl phosphonium tetrafluoroborate, 0.125 mmol), Mo(CO)$_6$ (molybdenum hexacarbonyl, 1.246 mmol), methylamine (1.5 equiv., 2N in THF) and DBU (1,8-diazabicyclo[5.4.0]undec-7-ene, 1.869 mmol). The reaction mixture was irradiated at 130° C. for 5 minutes in a microwave reactor. The reaction mixture was concentrated and then purified on column (silica gel, dichloromethane/methanol 98:2) to give 0.25 g (71%) of ethyl 4-[(4-methoxyphenyl)amino]-6-(methylcarbamoyl)quinoline-3-carboxylate. $^1$H NMR (300 MHz, CDCl$_3$) δ10.96 (s, 1H, —NH—) 9.24 (s, 1H, aromatic), 8.14-7.98 (m, 2H, aromatic), 7.73 (s, 1H, aromatic), 7.16 (d, 2H, J=9 Hz, aromatic), 6.98 (d, 2H, J=9 Hz, aromatic), 4.46 (q, 2H, J=7 Hz, —CH$_2$—), 3.87 (s, 3H, —OCH$_3$), 1.48 (t, 3H, J=7 Hz, —CH$_3$); LC-MS (m/z) 380.0 (M+1).

Example 4

4-[(4-Methoxyphenyl)amino]-6-(methylcarbamoyl)quinoline-3-carboxylic Acid

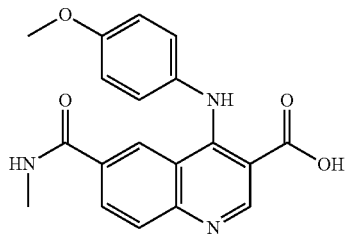 [SMILES: CNC(=O)c1ccc2ncc(C(=O)O)c(Nc3ccc(OC)cc3)c2c1]

Ethyl 4-[(4-methoxyphenyl)amino]-6-(methylcarbamoyl)quinoline-3-carboxylate (0.2 g) was stirred with LiOH (85.5 mg) in 6 mL of MeOH:THF:H$_2$O (2:2:2) overnight. The reaction mixture was concentrated and the aqueous layer was washed with ethyl acetate. The aqueous layers were collected and acidified with aqueous HCl and the precipitate formed was filtered and dried to give 0.142 g (60%) of 4-[(4-methoxyphenyl)amino]-6-(methylcarbamoyl)-quinoline-3-carboxylic acid. $^1$H NMR (300 MHz, CD$_3$OD) δ 9.05 (s, 1H, aromatic), 8.20 (s, 1H, aromatic), 8.12-7.81 (m, 2H, aromatic), 7.27 (d, 2H, J=9.9 Hz, aromatic), 7.06 (d, 2H, J=9.9 Hz, aromatic), 3.88 (s, 1H, —OCH$_3$), 2.82 (s, 3H, —NCH$_3$); LC-MS (m/z) 352.0 (M+1).

Example 5

Butyl 4-[(4-methoxyphenyl)amino]-6-(methylcarbamoyl)quinoline-3-carboxylate. (Intermediary Product)

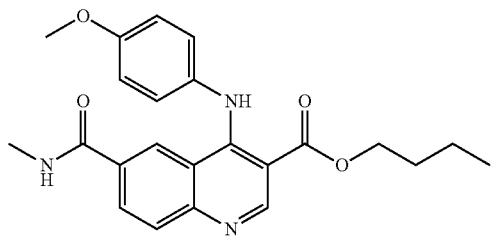 [SMILES: CCCCOC(=O)c1cnc2ccc(C(=O)NC)cc2c1Nc1ccc(OC)cc1]

To a suspension of 4-[(4-methoxyphenyl)amino]-6-(methylcarbamoyl)-quinoline-3-carboxylic acid (0.1 g) in dichloromethane EDC.HCl (1-Ethyl-3-(3-dimethyl-aminopropyl) carbodiimide hydrochloride, 0.161 g), HOBt (N-hydroxybenzotriazole 0.042 g), DMAP (4-dimethylaminopyridine, 0.17 g) and n-butanol (25 mL) were added, and the reaction mixture was stirred at room temperature for 3 hours. After aqueous work up, the reaction mixture was extracted, concentrated and dried over anhydrous sodium sulphate to afford the crude product which was later purified by column chromatography to afford 0.05 g (55% yield) of butyl 4-[(4-methoxyphenyl)amino]-6-(methylcarbamoyl)quinoline-3-carboxylate. $^1$H NMR (300 MHz, CDCl$_3$) δ 10.84 (s, 1H, —NH—), 9.21 (s, 1H, aromatic), 8.05 (d, 1H, J=8.8 Hz, aromatic), 7.97 (d, 1H, J=8.8 Hz, aromatic), 7.80 (s, 1H, aromatic), 7.16 (d, 2H, J=8.7 Hz, aromatic), 6.96 (d, 2H, J=8.7 Hz, aromatic), 5.60 (s, 1H, —NHCH$_3$—), 4.41 (t, 2H, J=6.6 Hz, —O—CH$_2$—), 3.87 (s, 3H, —OCH$_3$), 2.88 (s, 3H, —NCH$_3$), 1.92-1.75 (m, 2H, —O—CH$_2$—CH$_2$—CH$_2$—), 1.65-1.46 (m, 2H, —O—CH$_2$—CH$_2$—CH$_2$—), 1.12-0.98 (m, 3H, —CH$_3$); LC-MS (m/z) 407.9 (M+1).

Example 6

Methyl 4-[(4-methoxyphenyl)amino]-6-(methylcarbamoyl)quinoline-3-carboxylate. (Intermediary Product)

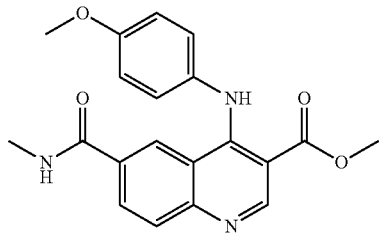

To a suspension of 0.1 g of 4-[(4-methoxyphenyl)amino]-6-(methylcarbamoyl)-quinoline-3-carboxylic acid in dichloromethane EDC.HCl (1-ethyl-3-(3-dimethyl-aminopropyl) carbodiimide hydrochloride, 0.161 g), HOBt (N-hydroxybenzotriazole, 0.042 g), DMAP (4-dimethylaminopyridine, 0.17 g) and 20 mL of methanol were added and the reaction mixture was stirred at room temperature for 3 h. After aqueous work up, the reaction mixture was extracted, concentrated and dried over anhydrous sodium sulfate to afford the crude product which was later purified by column chromatography to afford 0.062 g (60%) of methyl 4-[(4-methoxyphenyl)amino]-6-(methylcarbamoyl)quinoline-3-carboxylate. $^1$H NMR (300 MHz, CDCl$_3$) δ 11.51 (s, 1H, —NH—), 9.12 (s, 1H, aromatic), 8.38-8.15 (m, 2H, aromatic), 8.10 (s, 1H, aromatic), 7.23 (d, 2H, J=9 Hz, aromatic), 7.02 (d, 2H, J=9 Hz, aromatic), 4.02 (s, 3H, —OCH$_3$), 3.90 (s, 3H, —OCH$_3$), 2.92 (s, 3H, —NCH$_3$); LC-MS (m/z) 365.9 (M+1).

Biological Tests
Integrin Assay

This assay was conducted by Biodesy (Burlingame, Calif., USA). Purified integrins were obtained from academic and commercial sources. Alpha-5-beta-1 and alpha-v-beta-3 were obtained from academic sources as recombinant, soluble proteins (the extracellular domain).

A standard labeling protocol developed for integrins was applied to each of the three proteins. All proteins were successfully labeled with an average label:protein ratio of ~4:1. The two soluble, labeled proteins (alpha5beta1 and alphavbeta3) produced background SHG (second-harmonic generation) signals. They also produced conformational change signals upon exposure to GRGDSP (RGD-peptide, a fibronectin-derived peptide Gly-Arg-Gly-Asp-Ser-Pro). The peptide was added at 400 μM and signal changes were immediate (FIG. 1).

Next, Example 4 was pre-incubated at 100 μM with the labeled proteins for 20 minutes. RGD peptide was then added (400 μM) to stimulate the protein and to test each compound for inhibition.

Figure 2:
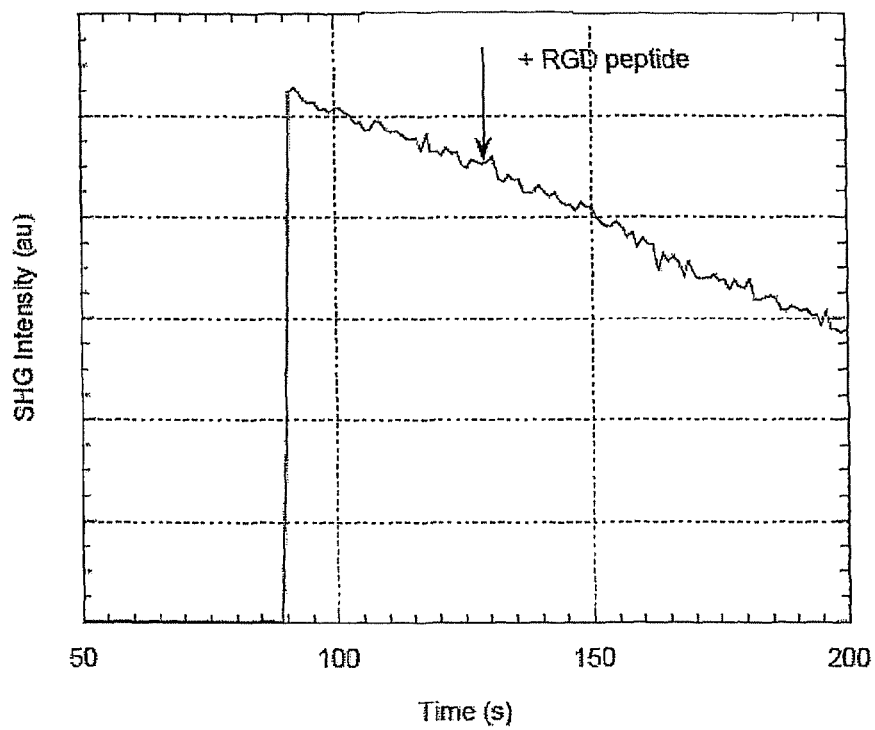
FIG. 2 is a plot of the SHG signal as a function of time, obtained from labeled alpha-5-beta-1 receptor (upper) and alpha-v-beta-3 (lower) in the presence of a compound of the invention and a peptide derived from fibronectin, indicating the inhibition (lack of conformational change) of alpa-5-beta-1 receptor by the compound of the invention, but not alpha-v-beta-3 (conformational change).
Figure 2:
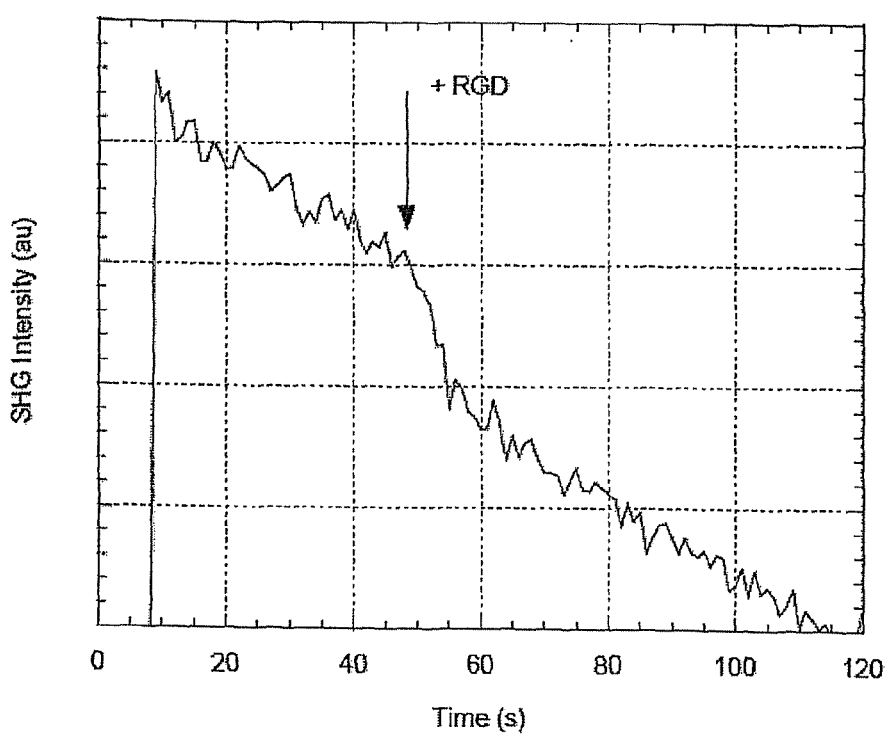

Example 4 prevented RGD-induced conformational change in alpha-5-beta-1 and is therefore an effective inhibitor of RGD-induced conformational change. On the other hand, Example 4 had no effect on alpha-v-beta-3, as a conformational change in the protein was evident (FIG. 2).

Tumor Xenograft Model

Figure 3:
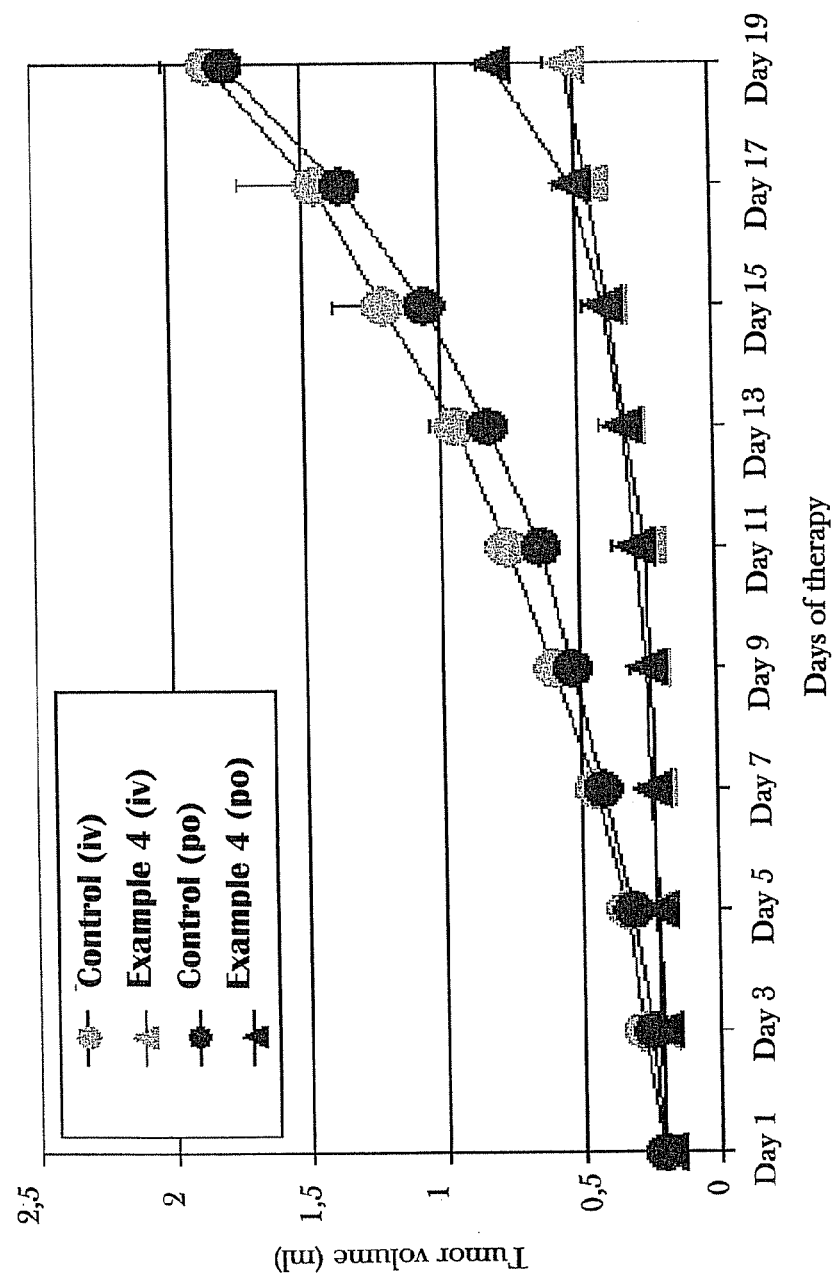
FIG. 3 is a plot of the tumor volume (ml) in mice having received subcutaneously implanted lung cancer cells, as a function of days of therapy by po and iv (25 mg/kg/day) administration of a compound of the invention, compared to administration of vehicle only.

Female 6-week-old SCID mice were used for tumor studies. Approximately $10^6$ human Calu-6 lung cancer cells growing in logarithmic phase were harvested and resuspended in media, and a single cell solution in a volume of 100 ml was implanted subcutaneously at the right flank of each animal. 10 mice were used in the treated groups and 10 mice were used in the control groups. Systemic treatment by oral administration or iv injections with either 100 ml of vehicle or active substance (25 mg/kg/day) was begun when tumors reached a size of 300 $mm^3$ and continued once daily for a total of 17 days. Visible tumors were present day 5-10 after implantation. Primary tumors were measured with digital calipers on the days indicated. Tumor volumes were calculated according to the formula: Length×$width^2$×0.52 as reported. Example 4 was administrated (iv and oral administration, 25 mg/kg/day) to the mice, which showed convincing results for the effectiveness of the compound in this animal model (FIG. 3). With an inhibition of tumor volume with 52% for oral treatment and 71% for iv treatment the compound of the invention has great anti-tumor effect. The compound of the invention also inhibits angiogenesis significantly in both groups.

Laser Induced Mouse Eye Model

Figure 4:
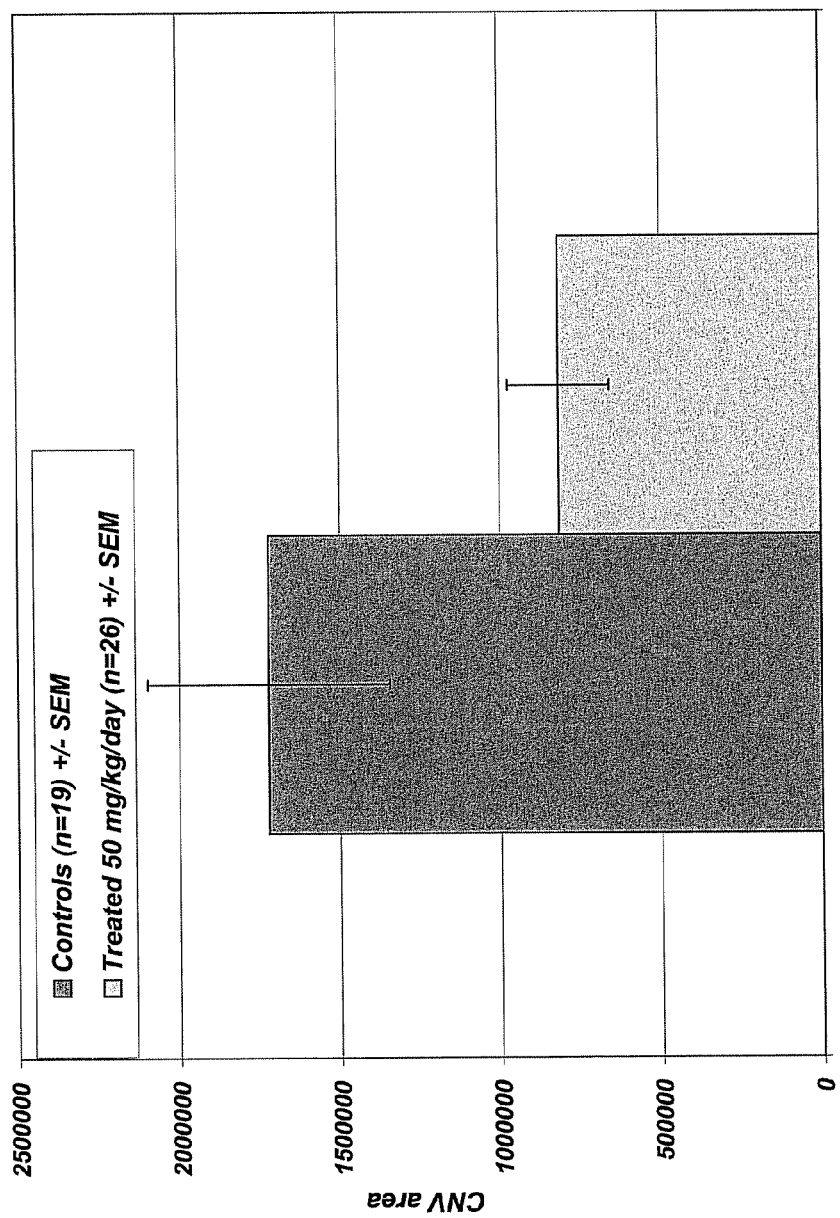
FIG. 4 is a bar chart representing the inhibition of laser-induced chorodial neovascularization (CNV) in mice given a compound of the invention at 50 mg/kg orally.
Figure 5:
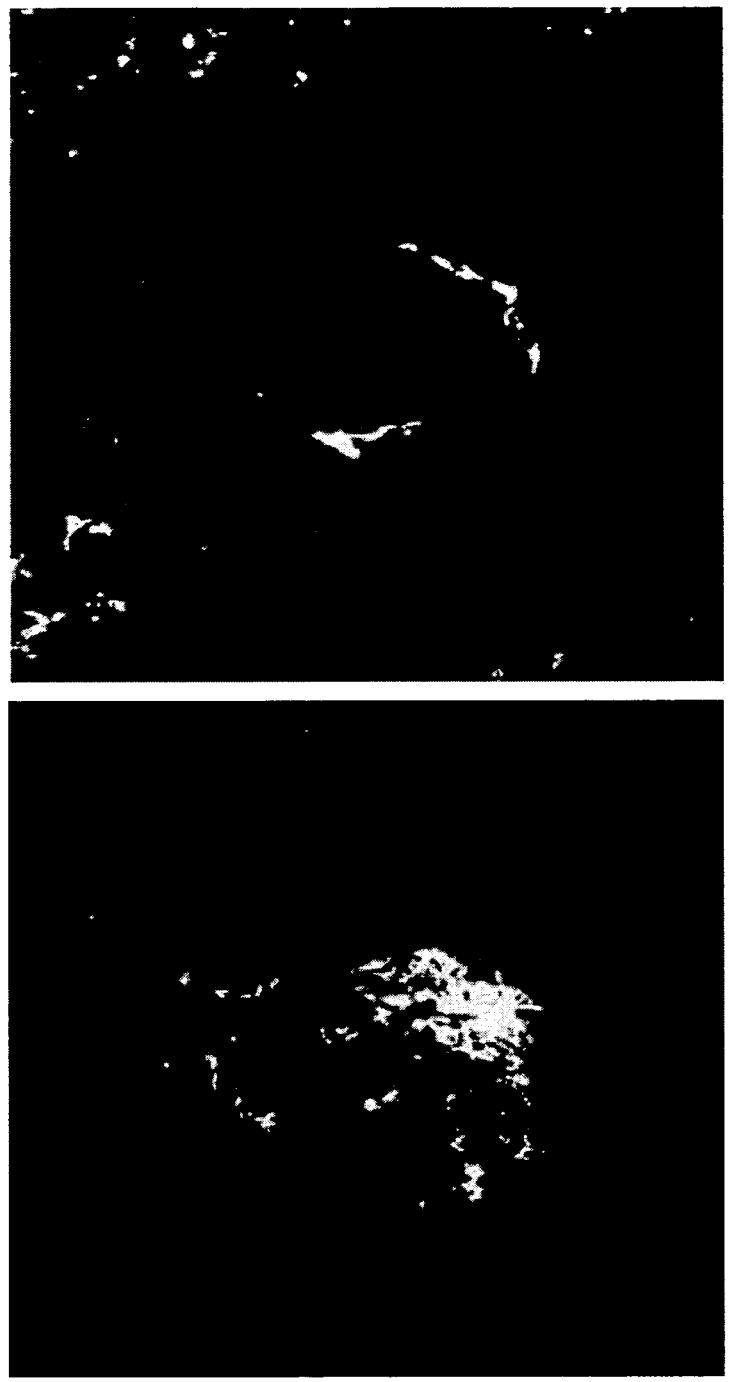
FIG. 5 is an image of retinal epithelium in laser induced CNV mouse model: The essentially circular area is the destroyed retinal pigment epithelium (RPE) and Bruchs membrane (BM). The white area shows the ingrowth of vessels into the laser spot. On the left, control retina with massive ingrowth of new vessels, on the right, retina with just a little (just at the edges) ingrowth of vessels, after treatment with inventive compound.

In this model Example 4, alone, inhibited the CNV (chorodial neovascularization) growth in eye significantly with 42% compared with control when given orally at 50 mg/kg/day (FIG. 4 and FIG. 5). This laser-induced model of CNV is a highly reproducible model that mimics many features of CNV occurring in the wet form of age-related macular degeneration (AMD), the leading cause of blindness in the elderly.

The invention claimed is:
1. The compound:

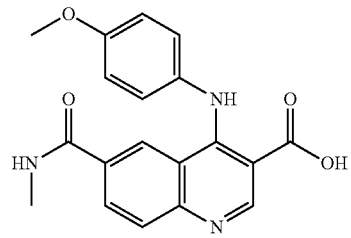 [SMILES: CNC(=O)c1ccc2ncc(C(=O)O)c(Nc3ccc(OC)cc3)c2c1]

4-[(4-methoxyphenyl)amino]-6-(methylcarbamoyl)quinoline-3-carboxylic acid, or a pharmaceutically acceptable salt thereof.

2. A pharmaceutical composition comprising a therapeutically effective amount of the compound according to claim 1, or a pharmaceutically acceptable salt thereof, and at least one pharmaceutically acceptable excipient.

3. The pharmaceutical composition according to claim 2, further comprising at least one additional pharmaceutically active compound.

4. The pharmaceutical composition according to claim 3, wherein the additional pharmaceutically active compound has anti-tumor activity.

5. A method of treating age-related macular degeneration, comprising administering an effective amount of the compound according to claim 1, or a pharmaceutically acceptable salt thereof, to a subject in need thereof.

6. A method of treating lung cancer, comprising administering an effective amount of the compound according to claim 1, or a pharmaceutically acceptable salt thereof, to a subject in need thereof.

* * * * *